(12) United States Patent
Wahli et al.

(10) Patent No.: US 8,518,459 B2
(45) Date of Patent: Aug. 27, 2013

(54) COMPOSITION FOR REGULATING LIPID METABOLISM

(75) Inventors: Walter Wahli, Echichens (CH); Marie Françoise Yvonne Bourgeois-Lugand, Loqueffret (FR); Bernadette Husson-Robert, Saint Apollinaire (FR); Gilles Didier Parisot, Ollon (CH)

(73) Assignee: Actigenomics S.A., Epalinges (CH)

( * ) Notice: Subject to any disclaimer, the term of this patent is extended or adjusted under 35 U.S.C. 154(b) by 0 days.

(21) Appl. No.: 13/138,881

(22) PCT Filed: Apr. 15, 2010

(86) PCT No.: PCT/IB2010/051653
§ 371 (c)(1),
(2), (4) Date: Oct. 14, 2011

(87) PCT Pub. No.: WO2010/119424
PCT Pub. Date: Oct. 21, 2010

(65) Prior Publication Data
US 2012/0034201 A1  Feb. 9, 2012

(30) Foreign Application Priority Data
Apr. 15, 2009  (WO) ............... PCT/IB2009/005239

(51) Int. Cl.
*A61K 36/00* (2006.01)
*A61K 36/63* (2006.01)
*A61K 36/03* (2006.01)
*A61K 36/8962* (2006.01)
*A61K 36/06* (2006.01)
*A61K 36/87* (2006.01)

(52) U.S. Cl.
USPC ........... 424/725; 424/520; 424/523; 424/766; 424/195.15; 424/754

(58) Field of Classification Search
None
See application file for complete search history.

(56) References Cited

U.S. PATENT DOCUMENTS

| | | |
|---|---|---|
| 2007/0196440 A1 | 8/2007 | Shulman et al. |
| 2008/0102111 A1 | 5/2008 | Imanaka |
| 2010/0215761 A1 | 8/2010 | Bourgeois-Lugand et al. |

FOREIGN PATENT DOCUMENTS

| | | |
|---|---|---|
| EP | 1857112 A1 | 11/2007 |
| EP | 2036444 A1 | 3/2009 |
| WO | WO-2004105770 A1 | 12/2004 |
| WO | WO-2006016363 A2 | 2/2006 |
| WO | WO-2009050580 A1 | 4/2009 |

OTHER PUBLICATIONS

International Search Report for International Application No. PCT/IB2010/051653 filed Apr. 15, 2010.
J. Plat et al., "Effects of plant sterols and stanols on lipid metabolism and cardiovascular risk," *Nutr. Metab. & Cardiovasc. Dis.*, vol. 11, No. 1, pp. 31-40 (Feb. 1, 2001) XP008037504.

*Primary Examiner* — Qiuwen Mi
(74) *Attorney, Agent, or Firm* — Harness, Dickey & Pierce, P.L.C.

(57) ABSTRACT

This invention concerns a nutraceutical and/or food composition for regulating, among other things, lipid metabolism in humans and animals, and methods of use of said nutraceutical and/or food composition.

13 Claims, 13 Drawing Sheets

After 12 Weeks of Treatment

After 12 Weeks of Treatment

COMPOSITION FOR REGULATING LIPID METABOLISM

FIELD OF THE INVENTION

This invention concerns a nutraceutical and/or food composition for regulating, among others, lipid metabolism in humans and animals, as well as methods that may be used in the food industry and/or nutraceutical field for that said composition.

DISCUSSION OF THE STATE OF THE ART

Dietary therapies are becoming essential in the regulation of lipid metabolism, and more specifically to cause a decrease in LDL-cholesterol and reduce the risk of coronary heart disease. To this end, in many countries, food enriched with plant sterols and stanols has been developed in parallel with the global development of coronary heart disease, major causes of morbidity and mortality.

Phytosterols:

Phytosterols (sterols and stanols from plants) are a dietary option available to reduce plasma cholesterol (TC) and LDL-cholesterol, since these biochemical effects have been shown in humans in the 1950s. Since then, numerous clinical studies have confirmed the results: mainly stanols and sterols esterified from vegetable oils (mainly C18 ones) significantly decrease TC and LDL-cholesterol when administered in the diet (Katan et al, 2003). Phytosterols at 2 g/day lower by 10% the levels of LDL-cholesterol. More than 40 plant sterols have been identified; sitosterol, campesterol and stigmasterol are the most abundant. Stanols (sitostanol and campestanol) are saturated sterols and are less common in nature than sterols.

While 50% of the cholesterol is absorbed in the intestinal tract, the intestinal absorption of stanols and sterols is much lower: 10-15% for campesterol and campestanol, 4-7% for sitosterol, and 1% for sitostanol. Stanols and sterols are hydrolyzed in the upper small intestine.

The main mechanism of action reducing cholesterol level with phytosterols and phytostanols is the inhibition of intestinal absorption of cholesterol, involving proteins of the "ATP-binding cassette" (ABC) G superfamily, especially ABCG5 and ABCG8.

The recommended daily intake of phytosterols for a 30 to 40% decrease of the intestinal absorption of cholesterol is 2 g (Katan et al, 2003; Trautwein et al, 2003), knowing that the ingested daily dose of plant sterols or stanols ranges from 0.150 to 0.450 mg/day.

The esterification of sitosterol or sitostanol with fatty acids increases both their solubility in mayonnaises and margarines, as well as their intestinal dispersion, thus maximizing their effectiveness.

The physical form of sterols and stanols is very important; free (i.e. non-esterified) sterols and stanols may have similar effects on plasma lipoproteins as esters (Katan et al, 2003); but the matrix and the emulsification process are very important and may bring negative results (Denke, 1995). Free stanols, emulsified with lecithin, reduce intestinal absorption by 37% in a single administration. There is no significant change in efficiency according to the dissolution of sterols/stanols in diacylglycerol or their incorporation into low-calorie products (low calorie bread, cereal or yogurt), even if the efficiency is lower with bread and cereals. However, the effects of dimethylsterols of rice bran on lipoproteins are lower than those of sterols issued from cholesterol, such as sitosterol In many clinical studies, the daily intake (2.5 g) of sterols or stanols is divided into 2 or 3 portions or as a single intake at lunch, in order to obtain the same effect on the reduction of LDL-cholesterol. The distribution of intake of sterols or stanols is not crucial to their effectiveness; the daily amount alone is what matters.

Sterols and stanols must lower cholesterol levels, in people under normal diet as well as in people under hyper-rich diet. Thus, phytosterols/stanols are complements for healthy diets low in saturated fatty acids and cholesterol, but also in diets enriched in fruits, vegetables, and oils as sources of fat.

Side Effects:

Stanols and sterols do not bring very serious side effects, and therefore the balance risk/benefit appears clearly favorable.

However, since sterols and stanols have been found in atheromatous plaques, it was suggested that the primary atherosclerosis in patients with homozygous phytosterolaemia is due to an atherogenic effect of circulating sitosterols and campesterols. However, the high rate of atherosclerosis in these phytosterolemic patients may be due to other genetic disorders.

Some experiments report that plant sterols and stanols have estrogenic effects; however, sterols do not bind to estrogen receptors.

Eighteen clinical studies have tested the dose of 1.5 g/day in stanols/sterols, and showed a significant reduction in plasma concentrations of carotenoids, including α-carotene (−9%), β-carotene (−28%), and lycopene (−7%). The decrease in β-carotene can be avoided by eating fruits or vegetables countervailing carotenoids (Clifton et al., 2004).

Furthermore, it is known that nutrients such as trace elements, plants, food principles (amino-acids) or vitamins can activate or inhibit certain functions of the body. Micronutrition, consisting in providing the body with one or more nutrients in small quantities, partially solved the problems of conventional nutrition, including the saturation of absorption sites in the intestine. Indeed, the micro-quantities of administered nutrients do not saturate the sites of intestinal absorption, and absorbed nutrients are then directly assimilated by the cells.

In particular, PCT/IB2008/002815 (Bioresearch & Partners) describes a composition, hereinafter defined under the name LIPISTASE composition, for the regulation of lipid metabolism, and methods used in the field of food, as well as in the nutraceutical and therapeutic fields. In particular, the invention involves food additives or supplements, a composition containing these and their uses thereof, in particular for revitalizing a subject's metabolism, in particular, that of human beings.

Despite the solutions proposed by the prior art, there is, however, no effective composition or food additive with no or few side or secondary effects on the body, and able to act at the same time on:

The side effects induced by large amounts of administered PS, and the frequency of their administration;
The familial dyslipidemia and dyslipidemia associated with metabolic syndrome;
The prevention of metabolic syndrome and type-2 prediabetes;
Cardiovascular disease, some cancers, and macular degeneration;
High blood pressure and thrombosis, atherosclerosis;
Neurodegenerative diseases, such as Alzheimer's disease.

BRIEF DESCRIPTION OF THE INVENTION

This invention proposes to meet this demand by developing an innovative nutraceutical and/or food composition for, among other things, the regulation of lipid metabolism in humans or animals.

More particularly, this invention concerns a nutraceutical and/or food composition comprising:

- 7 μg to 700 μg (per 100 g/100 ml) of at least two plant oils selected from among rapeseed oil, olive oil, grapeseed oil, and evening primrose oil,
- 10 μg to 1000 μg (per 100 g/100 ml) of positively charged minerals chosen from among sodium, magnesium, and calcium,
- 10 μg to 1000 μg (per 100 g/100 ml) of metals chosen from between zinc and iron,
- 7 μg to 700 μg (per 100 g/100 ml) of yeast or yeast extracts originating from the *Saccharomyces cerevisiae* genus, characterized in that said yeasts or yeast extracts are enriched with Selenium;
- 7 μg to 700 μg (per 100 g/100 ml) of mushrooms or Shiitake mushroom extracts (mycelium)
- 6 μg to 600 μg (per 100 g/100 ml) of at least two plant extracts from plants chosen from among samphire, garlic, and grapevine,
- 8 μg to 800 μg (per 100 g/100 ml) of at least one vitamin chosen among vitamins A, B1, B9, C, E, F, and PP
- 7 μg to 700 μg (per 100 g/100 ml) of animal oil and Copra oil (*Cocos nucifera*)
- 6 μg to 600 μg (per 100 g/100 ml) of at least one alga chosen among *Palmaria palmata* (Dulse), *Chondrus crispus* (Carrageen), and *Fucus vesiculosus* (Bladder wrack), in combination with one or more phytosterols, stanols or mixtures thereof, as well as a pharmaceutical acceptable excipient.

One or several phytosterols/stanols (referred to herein as the initials PS) and/or their mixtures, as well as said excipient will advantageously supplement the volume so as to obtain 100 ml of the pharmaceutical composition in accordance with the invention.

It has been shown that the nutraceutical and/or food composition according to the invention produces synergistic effects, and far superior to those of composition LIPISTASE only (PCT/IB2008/002815; Bioresearch & Partners) and phytosterols/stanols taken separately.

Other objects of the invention relate to methods:
For the regulation of lipid homeostasis
For the prevention of metabolic syndrome, cancer risks, cardiovascular diseases, dyslipidemia, hypertension, progression of atherosclerosis, obesity, hyperglycemia, macular degeneration in diabetes, and neurodegenerative diseases in humans and animals.

The use of said nutraceutical and/or food composition for the preparation of a medication for the treatment and/or prevention of metabolic syndrome, cancer risks, cardiovascular diseases, dyslipidemia, hypertension, progression of atherosclerosis, obesity, hyperglycemia, macular degeneration in diabetes, neurodegenerative diseases, and regulation of lipid homeostasis in humans and animals is also one of the objects of the present invention.

Other unexpected benefits of the nutraceutical and/or food composition according to the invention appear on reading the detailed description and examples of embodiments of the invention.

DETAILED DESCRIPTION OF THE INVENTION

Figure 1:
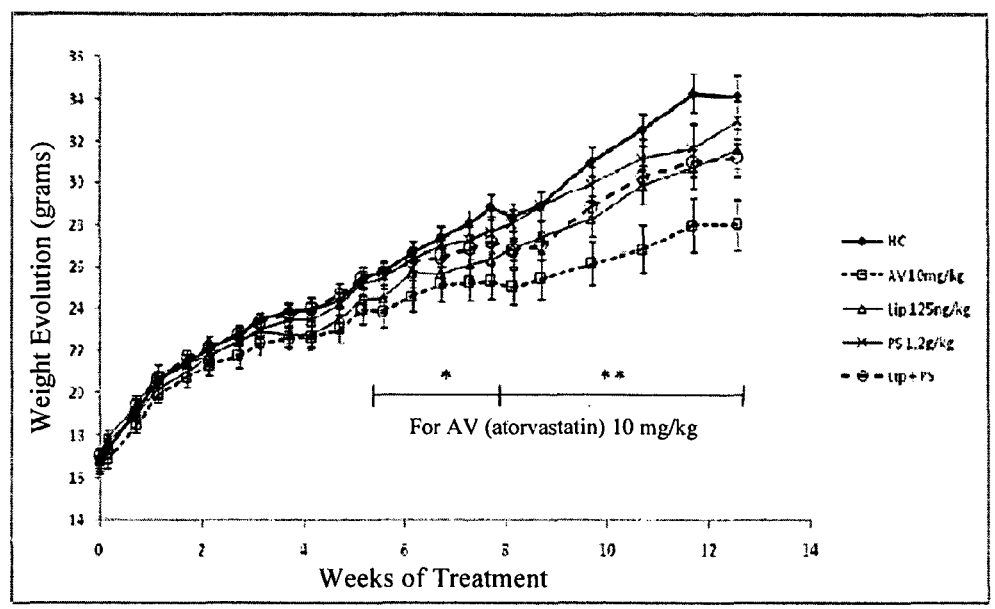
FIG. 1: Changes in body weight of C57B16J mice subjected to diet rich in cholesterol and under different treatments, expressed in g, *p n=12.

This invention concerns the implementation of a nutraceutical and/or food composition displaying properties which are particularly advantageous on the regulation of metabolism of lipids in humans or in animals.

One of the first objects of this invention is to provide a nutraceutical and/or food composition, comprising the combination of the LIPISTASE composition:

7 µg to 700 µg (per 100 g/100 ml) of at least two plant oils selected from among rapeseed oil, olive oil, grape seed oil, and evening primrose oil,
10 µg to 1000 µg (per 100 g/100 ml) of positively charged minerals chosen among sodium, magnesium, and calcium,
10 µg to 1000 µg (per 100 g/100 ml) of metals chosen from zinc or iron,
7 µg to 700 µg (per 100 g/100 ml) of yeast or yeast extracts originating from the Saccharomyces cerevisiae genus, characterized in that said yeasts or yeast extracts are enriched with selenium;
7 µg to 700 µg (per 100 g/100 ml) of mushrooms or Shiitake mushroom extracts (mycelium)
6 µg to 600 µg (per 100 g/100 ml) of at least two plant extracts from plants chosen among samphire, garlic, and grapevine,
8 µg to 800 µg (per 100 g/100 ml) of at least one vitamin chosen among vitamins A, B1, B9, C, E, F, and PP
7 µg to 700 µg (per 100 g/100 ml) of animal oil and Copra oil (Cocos nucifera)
6 µg to 600 µg (per 100 g/100 ml) of at least one alga chosen among Palmaria palmata (Dulse), Chondrus crispus (Carrageen), and Fucus vesiculosus (Bladder wrack), in combination with one or more phytosterols, stanols or mixtures thereof, as well as a pharmaceutical and/or alimentary acceptable excipient.

One or several phytosterols/stanols and/or their mixtures, as well as said excipient will advantageously supplement the volume so as to obtain 100 ml of the pharmaceutical composition in accordance with the invention.

It will be advantageous to use a legal amount of phytosterols or stanols according to the allowed range between 1.6 and 3.3 g/day. The recommended amount of phytosterols or stanols or their mixture is preferably between 2 and 2.4 g/day (I Demonty, R T Ras, H C M Van der Knaap, G Duchateau, L Meijer, P L Zock, J M Geleijnse, E A Trautwein, "Continuous dose-response relationship of the LDL-cholesterol-lowering effect of phytosterol intake", J Nutr 139, 271-284, 2009).

According to a particular embodiment of the invention, the PS used are preferably selected from the group including: cholesterol, brassicasterol, campesterol, campestanol, stigmasterol, beta-sitosterol, beta-sitostanol, D5 avenasterol, D7 stigmastenol, D7 avenasterol, or their combinations and mixtures. Preferably, a mixture of the PS mentioned above will be used.

According to a preferred embodiment of the invention, the preparation of PS (phytosterols and stanols) will be advantageously created in the following proportions: cholesterol 0.4%, brassicasterol 3.2%, campesterol 27.2%, campestanol 0.7%, stigmasterol 15.4%, beta-sitosterol 47%, beta-sitostanol 1%, D5 avenasterol 1.9%, D7 stigmastenol 0.4%, D7 avenasterol 0.2%, unidentified sterols 2.6%.

Preferably, the nutraceutical and/or food composition of the invention comprises cold water fish oil (oleum piscis mare fresco) as animal oil.

In a preferred embodiment, the nutraceutical and/or food composition according to the invention contains at least two vitamins chosen among vitamin A, B1, B9, C, E, F and PP.

More particularly, the nutraceutical and/or food composition of the invention preferably comprises:

7 µg to 700 µg (per 100 g/100 ml) of rapeseed oil, olive oil, grape seed oil, and evening primrose oil,
10 µg to 1000 µg (per 100 g/100 ml) of sodium, magnesium, and calcium,
10 µg to 1000 µg (per 100 g/100 ml) of zinc and iron,
7 µg to 700 µg (per 100 g/100 ml) of Saccharomyces cerevisiae yeast or yeast extracts, enriched with selenium,
7 µg to 700 µg (per 100 g/100 ml) of mycelium or Shiitake mycelium extracts,
6 µg to 600 µg (per 100 g/100 ml) of samphire, garlic, and grapevine,
8 µg to 800 µg (per 100 g/100 ml) of vitamins A, B1, B9, C, E, F, and PP,
7 µg to 700 µg (per 100 g/100 ml) of cold water fish oil and Copra oil,
6 µg to 600 µg (per 100 g/100 ml) Palmaria palmata (Dulse), Chondrus crispus (Carrageen), and Fucus vesiculosus (Bladder wrack), in combination with one or more phytosterols, stanols or mixtures thereof, as well as a pharmaceutical acceptable excipient.

Preferably, the nutraceutical and/or food composition of the invention may include excipients or additives, for example: water, oil, lactose-saccharose or lactose-starch, fructo-oligosaccarides, sorbitol, dicalcium phosphate or, among the excipients used in foods (as food additives),: dyes, preservatives (potassium sorbate, sodium benzoate), flavors, antioxidants (carotenoids, vitamins C and E, flavonoids), emulsifiers (lecithin, mono and di-glycerides of fatty-acids), stabilizing and gelling agents (lecithin, potassium lactate, agar agar, carrageenans, sodium alginate), flavor enhancers (glutamic acid salts, sodium inosinate), acidifiers (citric acid, sodium malate), anti-caking agents (magnesium stearate, silicon dioxide), sweeteners (sorbitol, sodium saccharin).

The composition according to the invention preferably includes at least two oils chosen among rapeseed oil, olive oil, grape seed oil, and evening primrose oil. Advantageously, the composition should include at least three plant oils, more preferentially it includes rapeseed oil, olive oil, grape seed oil, and evening primrose oil.

98% of rapeseed oil (Oleum Brassica napus oleifera) is made up by fatty acid triesters; the remaining 2% is rich in sterols and tocopherols (of which vitamin E). It is an oil rich in alpha-linoleic acid, omega-3 poly-unsaturated fatty-acids, omega-6 mono-unsaturated fatty-acids (with an interesting Omega 3:6 ratio of 1:2.5); and only 6 to 8% of saturated fatty-acids.

Olive oil (Oleum Olea europaea) is an oil rich in oleic acid: mono-unsaturated fatty acids (>75%), Omega 6 (8%); olive oil contains vitamins A, E and K. The ratio of vitamin E/PUFA (Poly Unsaturated Fatty Acids) is the highest of all oils.

Grape seed oil (Oleum Vitis vinifera) is an oil with balanced linoleic acid (alpha-linoleic and beta-linoleic), oleic, palmitic and stearic acids. This oil contains more than 70% of Omega-6. It is strongly unsaturated: the ratio of poly-unsaturated/saturated is >5.

Evening primrose oil (Oleum Oenotherae biennis) is an Omega-6 oil balanced in linoleic acid, gamma-linoleic acid, and oleic and stearic acids.

In one particular embodiment, the nutraceutical and/or food composition according to the invention includes rapeseed oil, olive oil, grape seed oil, and evening primrose oil.

Preferably, the minerals include one or more positively charged minerals, preferably chosen among sodium, magnesium, and calcium.

Sodium allows acid-base regulation and cellular metabolism of the body. It plays a determining role in cellular depolarization which is at the root of impulse excitability and conduction (in particular the neuromuscular and cardiac impulses), in maintaining acid-base balance, osmotic pressure, and in the balance between the body's liquid and ionic exchanges.

Magnesium is essential to the balance of the ionic channels. It acts as enzymatic cofactor and modulates the sodium ($NA^+$) and potassium ($K^+$) transport systems in all tissues; it is the physiological regulator of calcium in the balance of cellular exchange. Magnesium plays a role in stabilizing the different intracellular organelles: it stabilizes ribosomes that produce proteins, maintains the production of energy by the mitochondria because it is essential to the synthesis of ATP molecules. This production of energy is the basis for all cell life mechanisms and the overall vitality of the body. Magnesium is essential to the synthesis of proteins fundamental to cellular construction (certain amino-acids, DNA and RNA).

Calcium is involved in many enzymatic reactions. It allows the transmission of information at the cellular level as a second messenger which induces the transmission of the nerve impulse, the muscle contraction (by the movement of actin and myosin fibers), the stimulation of hormonal secretions by certain cells (such as insulin secretion by β pancreatic cells), and the release of neurotransmitters in the central nervous system.

In one particular embodiment, the nutraceutical and/or food composition according to the invention includes sodium, magnesium, and calcium.

Preferably the metals should include one or more metals chosen from either zinc or iron. Zinc intervenes in the activity of almost 200 enzymes [in particular in enzymatic systems like oxidoreductases, alcohol dehydrogenase, cytochrome reductase, and SOD (Superoxidismutase)]. Enzymes that are linked to zinc are significantly important in metabolic processes: glycolysis, pentose pathway, neoglucogenesis, lipid and fatty acid metabolisms.

Zinc is a metal activator for the majority of the coenzymes necessary for energy metabolism. Zinc plays a very important role in acid-base balance (carbonic anhydrase), in inflammation, cellular differentiation, and in the endogenous defense against free radicals. Zinc is also a hormonal cofactor (growth hormone, thyroid, adrenal cortex) and is essential to the transcription of the DNA chain (RNA-polymerase).

Zinc stabilizes cellular membranes by coupling with thiol groups, thus preventing their reaction with iron, thus avoiding production of hydrogen dioxide ($H_2O_2$), very unstable free radical. In particular, it intervenes in the metabolism of vitamin A (mobilization at the level of the liver, formation of retinol).

It stabilizes the protein structures and plays a role in gene expression.

As a component of the cytochromes, iron is essential to the detoxication and the production of thyroid hormones. Additionally, it binds with certain protein active sites which play an important role in the body: hemoglobin, myoglobin, and cytochromes.

In one particular embodiment, the nutraceutical and/or food composition according to the invention includes zinc and iron.

The yeast or yeast extracts are preferably yeasts of the Saccharomyces genus, or are extracts of these yeasts (for example, membrane, vesicle, protein preparations, etc. . . . ). They are particularly yeasts (or extracts) of the genus *Saccharomyces cerevisiae*.

In one particular embodiment, (extracts of) yeasts enriched with selenium are used, because of its antioxidant properties.

Other yeasts of the Saccharomyces genus or others (*Aspergillus, Torulospora* . . . ) may also be used, such as:
*saccharomyces boulardii* (used in food industry)
*saccharomyces cerevisiae* ("high fermentation" for wine, beer)
*saccharomyces uvarum* ("low fermentation" for Lager-type beers)
*schizosaccharomyces pombe* (African beer)
*aspergillus* (sake) inducing an alcoholic fermentation
*torulaspora delbrueckii* and *candida stellata* (initially present in must): allowing an increase in esters and a reduction in the formation of volatile acid.

Plant extracts preferably including one or more plant extracts. More preferably, the composition according to the invention includes, as a plant extract, at least two plant extracts selected among samphire, garlic, and grapevine.

Advantageously, the nutraceutical and/or food composition according to the invention includes samphire, garlic, and grapevine.

The term plant "extract" indicates, within the meaning of this invention, any preparation obtained from the entire or part of the plant in question. It can be a homogenate, a filtrate, seeds, leaves, stems, bark, etc, or combinations thereof. The extract can be prepared by traditional techniques.

Samphire (*Crithmum maritimum*) is very rich in minerals: zinc, iron, magnesium, copper, and manganese, and in vitamins A, E, B1, and B2. It has a detoxifying action.

Garlic (*Allium sativum*) is rich in vitamin C, zinc, manganese, and has a cholesterol-lowering action. Garlic is characterized by the presence of original sulfur substances (allyl trisulphide, (E)-ajoene) with beneficial effects on blood fluidity (reduces platelet aggregation) and blood cholesterol level (reduces the synthesis of triglycerides): of interest at the cardiovascular level. Other properties are attributed to garlic: antibacterial, antifungal, and antiviral. The organosulfur compounds inhibit carcinogen activation and contribute to the development of multidrug resistance. Liver and kidney protection against oxidative stress is also reported.

Grapes or grapevines (*Vitis vinifera*) are very rich in vitamins A and B and mineral salts: manganese, potassium, calcium. Grapes, rich in anti-radical substances, ease: detoxification/draining by the gall bladder and the liver.

The composition in accordance with the invention includes at least one alga or an extract of alga chosen among *Palmaria palmata* (Dulse), *Chondrus crispus* (Carrageen) and *Fucus vesiculosus* (Bladder wrack).

Dulse (*Palmaria palmata*) is very rich in provitamin A (a potent antioxidant, strengthening the immune system, and reducing tumor development) and in vitamin C (antioxidant, required in the synthesis of collagen, red blood cells, stimulates the immune system, promoter of iron absorption). Rich in essential amino acids and metals [copper ($Cu^{2+}$), nickel ($Ni^{2+}$), cadmium ($Cd^{2+}$) and zinc ($Zn^{2+}$)].

Bladder wrack (*Fucus vesiculosus*) is rich in fucosterol: a sterol which presents properties for lowering lipids like the plant beta-sitosterol. It is also very rich in iodine and iron.

Carrageen (Irish moss—*Chondrus Crispus*) is rich in fatty-acids and balanced between omega-3 and omega-6 fatty-acids, as well in unsaturated fatty-acids allowing the assimilation of cholesterol. It is also rich in amino-acids and trace elements (especially iodine, zinc, and iron); and in vitamin D.

In one particular embodiment, the composition includes extracts of *Palmaria palmata* (Dulse), *Chondrus crispus* (Carragaeen), and *Fucus vesiculosus* (Bladder wrack).

The pharmaceutical composition in accordance with the invention includes at least one mushroom or Shiitake mushroom (mycelium) extract. The Shiitake mycelium (*Lentinus edodes*) is very rich in amino-acids, trace elements, and vitamins. It presents cholesterol-lowering and immune system stimulating properties.

In a preferred embodiment, the vitamins include one or more vitamins chosen among vitamins A, B1, B9, C, E, F, and PP. In a preferred embodiment, the composition includes at least two different vitamins, more preferentially at least three, four, five or six different vitamins, chosen among the vitamins indicated above.

Vitamin A (retinol) is esterified inside the enterocyst, incorporated to chylomicrons, then excreted in the lymph from which it enters the general circulation through the lymphatic vessel. Vitamin A stabilizes cell membranes, biosynthesis and regulation of steroid hormones. Its effects on rod-shaped cells of the retina are essential for vision. The synthesis of certain proteins is also dependant on vitamin A.

Vitamin B1 (thiamin) provides sterols and fatty-acids to the cell in NADPH2 acid increases the intracellular formation of NADPH2, which is of paramount importance for the synthesis of lipids, sterols and fatty acids from sugars. It is essential to functioning of the nervous (degradation of pyruvic acid) and muscular systems.

Vitamin B9 (folic acid) is a coenzyme involved in the synthesis of purines and pyrimidines, constituents of nucleic acids (DNA and RNA). This vitamin is also involved in the synthesis of amino-acids (methionine, histidine, serine).

Vitamin C (ascorbic acid), enzyme cofactor, is required in the synthesis of collagen and red blood cells, and helps the immune system. It promotes iron absorption and metabolism. Carried to the brain in oxidized form, it is an antioxidant and reduces free radicals. It is involved in lipid metabolism, in association with various hydroxylases. The microsomal cytochrome P450-dependent hydroxylases act as a catalyst in the transformation of cholesterol into biliary acids in the presence of ascorbic acid.

Vitamin E (alpha-tocopherol) accompanies chylomicrons within the lymphatic vessels until reaching general circulation. In plasma, alpha-tocopherol is linked to several lipoprotein categories: LDLs which contain between 40 and 60% of it and HDLs which contains 35% of it. The vitamin E level is strongly related to that of the total lipids and of cholesterol. It has an antioxidant effect and reduces free radicals. It takes part in the formation and structure of membrane phospholipids, and thus has a stabilizing effect on cell membranes.

Vitamin F is one of the fat-soluble vitamins and is composed of polyunsaturated fatty acids, mainly linoleic acid. This fatty acid (a precursor of certain anti-inflammatory molecules) is essential for the synthesis of cholesterol and certain other fatty acids, and helps to maintain the integrity of cell membranes. Thus, vitamin E has a crucial role in the formation of the lipid barrier of the epidermis.

Vitamin PP [Vitamin B3, nicotinamide (niacin)], a precursor of NAD and NADP (2 cofactors involved in redox reactions), is essential for the metabolism of sugars, lipids and proteins. It plays a role in the formation of red blood cells, blood circulation, transport of oxygen to the cells, and the functioning of the digestive and nervous systems. It is also necessary for the synthesis of sex hormones and the production of neurotransmitters. It also has a cholesterol-lowering effect (by stimulating the lipase protein or by inhibiting lipolysis mediated by cyclic-AMP in adipose tissue).

In one particular embodiment, the composition according to the invention includes vitamin A, vitamin B1, vitamin B9, vitamin C, vitamin E, vitamin F, and vitamin PP.

Additionally, in a preferred embodiment, the composition of the invention also includes animal oil, especially fish oil, in particular cold water fish oil (*oleum pisci mare fresca*). This oil is rich in Omega 3 fatty-acids which reduce the blood level of triglycerides (by decreasing their hepatic synthesis), in particular VLDL. Omega-3s allow good membrane fluidity.

In addition, in one particularly preferred embodiment, the composition of the invention also includes Copra (*Cocos nucifera*). Copra is rich in fatty-acids and represents an intestinal regulator.

One object of the invention thus concerns a composition including rapeseed oil, olive oil, grape seed oil, evening primrose oil, cold water fish oil, Copra, sodium, magnesium, calcium, zinc, iron, an (extract from) *Saccharomyces cerevisiae* yeast(s), preferably enriched with selenium, plant extracts from samphire, garlic, *Palmaria palmata* (Dulse), *Chondrus crispus* (Carragaeen), *Fucus vesiculosus* (Bladder wrack), Shiitake (mycelium) and grapevine, vitamin A, vitamin B1, vitamin B9, vitamin C, vitamin E, vitamin F, and vitamin PP.

Depending on the family of ingredients, the preferred quantities of the nutraceutical and/or food composition according to the invention are determined for:
  plant oils (rapeseed oil, olive oil, grape seed oil, evening primrose oil): 28 µg to 280 µg/100 g or 100 ml
  trace elements: minerals (sodium, magnesium, calcium) and metals (zinc and iron): 40 µg to 400 µg/100 g or 100 ml
  *Saccharomyces cerevisiae* yeasts or yeast extracts, preferably enriched with selenium: 28 µg to 280 µg/100 g or 100 ml
  mushrooms or mushroom extracts (Shiitake mycelium): 28 µg to 280 µg/100 g or 100 ml
  marine algae or their extracts *Palmaria palmata* (Dulse), *Chondrus crispus* (Carrageen), and *Fucus vesiculosus* (Bladder wrack): 24 µg to 240 µg/100 g or 100 ml
  cold water fish oil and Copra: 28 µg to 280 µg/100 g or 100 ml
  plant extracts (samphire, garlic, and grapevine): 28 µg to 280 µg/100 g or 100 ml
  vitamins (A, B1, B9, C, E, F et PP): 32 µg to 320 µg/100 g or 100 ml,
in combination with one or more phytosterols, stanols or mixtures thereof, as well as a pharmaceutical acceptable excipient.

The invention may be implemented in any mammal, in particular in humans, adults, the elderly or in children.

The daily amount of the nutraceutical and/or food composition to be administered, ingested or applied to an individual may be subject to variations depending on the individual (age, sex, health condition, etc.). It is up to health professionals, and other specialists to adjust this amount according to the individual parameters to be taken into account.

As indicated previously, the nutraceutical and/of food composition in accordance with the invention presents advantageous properties for regulating lipid metabolism in humans or animals.

One object of the invention, in particular, concerns a method for the lipid metabolism in subjects, including the administration, application, or ingestion of a nutraceutical and/or food composition as defined in this invention.

This administration can be performed sequentially (LIPISTASE composition+phytosterols/stanols) or concomitantly (nutraceutical and/or food composition).

The nutraceutical and/of food composition can also be used as medication.

One object of this invention in particular is the use of nutraceutical and/or food composition for the preparation of a food additive for the regulation of lipid homeostasis and the prevention of metabolic syndrome, risk of cancers, cardiovascular diseases, dyslipidemia, hypertension, progression of atherosclerosis, obesity, hyperglycemia, macular degeneration of diabetes, neurodegenerative diseases in humans and animal.

In addition, the nutraceutical and/or food composition in accordance with the invention can also be used for the preparation of a medication to treat or prevent metabolic syndrome, cancer risks, cardiovascular diseases, dyslipidemia, hypertension, the formation of atheromatous plaques, progression of atherosclerosis, obesity, hyperglycemia, macular degeneration caused by diabetes, neurodegenerative diseases as well as regulation of lipid homeostasis in humans and animals.

The term "metabolic syndrome" indicates a set of metabolic disturbances (hypertension, hypertriglyceridemia, hypoHDL-cholesterol, hyperglycemia and obesity) that strongly predispose to the development of type-2 diabetes, cardiovascular diseases (atherosclerosis, coronary heart diseases), cerebrovascular diseases (stroke and degenerative central), endocrine disorders (infertility, impotence), cancers . . . .

High concentrations are needed to obtain significant effects on lipid profiles during administration of phytosterols and/or stanols (PS). The LIPISTASE composition significantly reduces lipid parameters with different mechanisms of action than those of PS (intestinal absorption of cholesterol). Thus, the addition of these two mechanisms of action by a joint administration of the composition LIPISTASE with PS (nutraceutical and/or food composition according to the invention) can reduce the amount of PS administered to achieve a better effect on lipids. In addition, the frequency of administration of PS can be reduced to a single one with the same results on lipids. Finally, by reducing the quantities of PS administered, not only are the risks of therapeutic drugs/PS intestinal interferences reduced, but also the effects on intestinal absorption.
   In certain animal experiments, administration of PS tends to increase plasma triglycerides. The LIPISTASE composition tends to reverse this effect and thus potentiates the activity of PS on lipid homeostasis for patients with dyslipidemia.
   No obvious effects on body weight have been reported in the literature. The LIPISTASE composition added to PS (nutraceutical and/or food composition according to the invention) allows animals to lose weight significantly. Thus, administration in humans of the nutraceutical and/or food composition according to the invention enables the prevention of metabolic syndrome in young patients and adults.
   PS significantly decreased plasma levels of carotenes. In parallel, low levels of carotenoids are associated with a significant risk of chronic diseases such as cardiovascular diseases, some cancers, and macular degeneration.

Anti-thrombotic and antioxidant effects observed with the nutraceutical and/or food composition according to the invention can unexpectedly slow down the apoptosis of endothelial cells, stimulate the functionality of the pericytes, improve microcirculation and blood pressure and also optimize the nutritive blood flow to peripheral tissues.

The LIPISTASE composition (via adiponectin) acts partially by activating AMP kinase. The tumor suppressor LKB1 is a regulator of the AMP kinase and stimulation of this activity can have an antitumor effect.

Considering these results, it was shown that the nutraceutical and/or food composition according to the invention lowers risks of cancers, of cardiovascular diseases in advanced metabolic syndrome, and prevents macular degeneration observed in diabetic patients.

In addition, PS, with no significant effect on atherosclerosis reported in humans, are gaining more power in combination with the LIPISTASE composition, and thus the nutraceutical and/or food composition according to the invention shows greater effects against the progression of atherosclerosis.

The LIPISTASE composition can increase a number of genes in the brain (ApoE, ABCA1, HMG-CoA reductase . . . ). Sterols, in turn, are supposed to be natural activators of LXRs, regulating cholesterol homeostasis. The nutraceutical and/or food composition according to the invention provides a more sustained modulation of cholesterol and fatty acids metabolism, and plays an important role in neurodegenerative diseases such as Alzheimer's disease.

The invention is described in more detail through the examples below. Other aspects and advantages of this invention will become apparent upon reading these examples, which must be regarded as illustrative and nonrestrictive.

EXAMPLES

Studies in Animals

Example 1

Protocol of Preparation

Five or six C57bl6J male mice (8 weeks of age) from breeding company Janvier (Le Genest Saint Isle, France) are distributed in cages and housed in a room with controlled humidity and temperature (23±0.5° C.). They are subject to a 12/12-hr light cycle (light at 7 am). During one week of adaptation, the animals have free access to drinking water and food, and are then randomized into 5 groups of 12 animals using as selection criteria weight, triglyceridemia and cholesterolemia.

The various groups formed are:
   a control group receiving a diet enriched in cholesterol (see composition in Table 1)
   a group treated with the reference, atorvastatin, 10 mg/kg/day,
   a group receiving a 125 ng/kg/day concentration of Lipistase,
   a group receiving PS (a mixture of phytosterols and stanols) to the total dose of 1.2 g/kg/day,
   a group receiving a combination of Lipistase and phytosterols.

All products (reference, study products and combination of products) are administered in the diet enriched in cholesterol, and administration to animals lasts three months. Lipistase, being in the form of a soybean oil suspension, all diets receive the same volume (1.8% w/w) of neutral soybean oil than that required to provide the desired amount of Lipistase.

TABLE 1

| Composition of "Western Diet", food enriched in cholesterol (U8958 version 8, Safe, Augis, France) | |
|---|---|
| Casein | 19.5% |
| PM 205B Safe | 7% |

TABLE 1-continued

Composition of "Western Diet", food enriched in
cholesterol (U8958 version 8, Safe, Augis, France)

| | |
|---|---|
| PV 200 Safe | 1% |
| Maltodextrin | 10% |
| Saccharose | 31% |
| Corn dextrin | 5.0% |
| Methionine (DL) | 0.3% |
| Dairy butter | 21% |
| Cellulose | 5.05% |
| Cholesterol | 0.15% |

The assessment of weight and food intake is carried out once a week. Every 4 weeks, a blood sample (retro-orbital sinus) allows tracking changes in cholesterolemia, triglyceridemia and glycemia.

Euthanasia is performed after 3 months of treatment (12 weeks). A blood test is performed, and the following parameters are measured on an automated Konelab (Thermo Fisher, France): total cholesterol (Thermo Fisher, 981,813), triglycerides (Thermo Fisher, 981,786), glucose (Thermo Fisher, 981,780), ALAT (Thermo Fisher, 981,769), ALP (Thermo Fisher, 981,771), ASAT (Thermo Fisher, 981,771).

The determination of lipoprotein profiles is carried out by FPLC (Synelvia, France) after two and three months of treatment and the amounts of cholesterol and triglycerides are measured in the different fractions (HDL, LDL and VLDL).

The dosages of insulinemia (Mercodia, Sweden, ref 10-1150-10), adiponectin (Biocat, Germany, ref K1002-1), and thyroxine (Genway, United States, ref 40-101-325036) are performed after 12 weeks of treatment.

Animals are sacrificed by cervical dislocation; liver, muscles (gastrocnemius and soleus), heart are quickly dissected, weighed and frozen in liquid nitrogen, then stored at −80° C. The various deposits of fat tissues (subcutaneous, peri-renal, inguinal and mesenteric) are removed and weighed to calculate the adiposity index.

Morphometric studies of adipose tissue are performed on 10 sections of each tissue (subcutaneous and perirenal) of all animals (n=12). For each section, 100 adipocytes are measured (perimeters and areas) and the values obtained are processed by the morphometry software Morpho-Pro (Exploranova).

Liver histological studies were carried out on 6 animals of each lot randomly chosen from their group. The median lobes of livers were removed and fixed in formalin, then included. For each animal, 30 sections are kept and stained with red oils to visualize lipid accumulations.

All data are presented with mean and SDOM (Standard Deviation of the Means). Statistical tests used are one-factor analysis of variance, followed by Bonferroni's test; differences at $p<0.05$ are considered significant. In some cases, Grubb or Dixon tests are carried out to identify and exclude outliers at $p=0.05$.

Example 2

Figure 2:
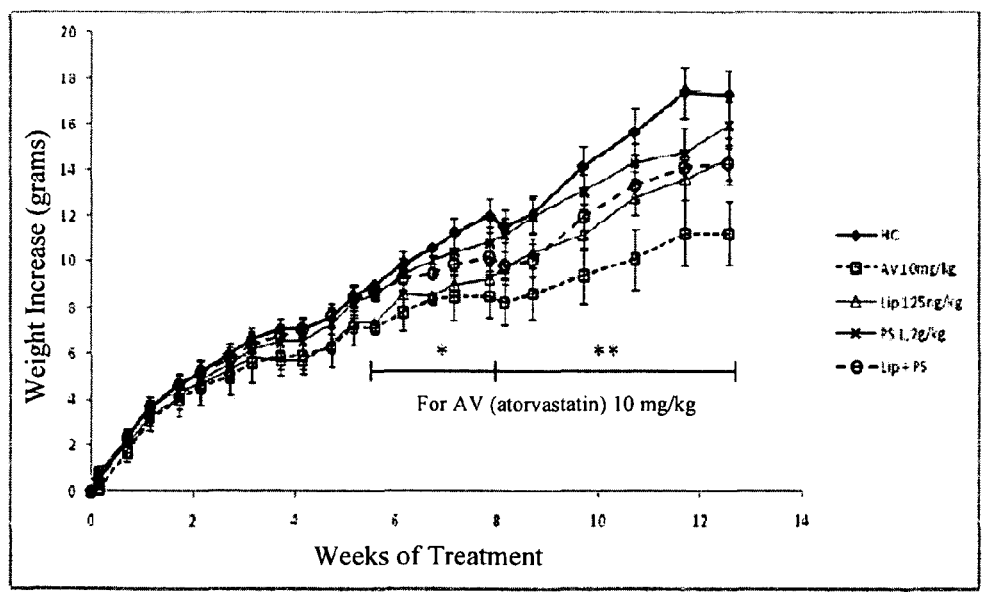
FIG. 2: Weight gain in C57B16J mice submitted to diet rich in cholesterol, and effect of different treatments, expressed in g, *p<0.05, n=12
Figure 3:
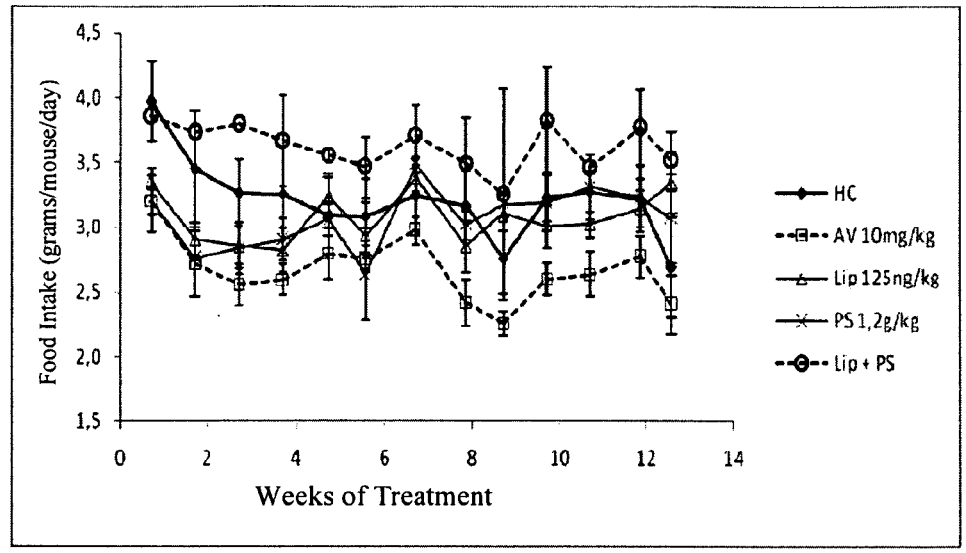
FIG. 3: Food intake, consumption in g per day per mouse, n=12
Figure 4:
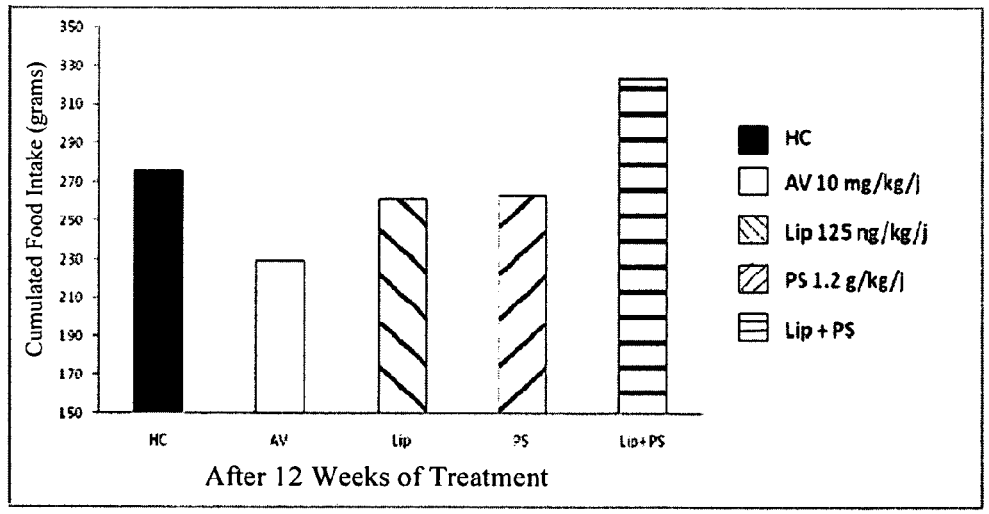
FIG. 4: Cumulative food intake per mouse after 12 weeks of treatment, expressed in g.

Demonstration of Synergy of the Combination Lipistase-Phytosterols/Stanols (PS) on Body Weight and on Changes in Lipid Distribution in the Body: Prevention of Overweight and Obesity FIG. 1 shows the evolution of body weight of mice regardless of the treatment. Only the reference has a weight significantly lower than the weight of control animals. However, in FIG. 2 expressing the evolution of weight gain, it is clear that Lipistase tends to reduce weight gain, and when combined with PS devoid of this tendency, it keeps the protective effect against weight gain. The effect of atorvastatin on the reduction of weight gain results from a reduction in food intake (FIG. 3), while this is not the case for either Lipistase alone or in combination with PS. Thus, if one considers the cumulative food intake reported in FIG. 4, animals receiving the combination Lipistase-PS consume 323 g while those receiving the PS (263 g) and Lipistase (260 g) have an intake very close to the value ingested by control animals (275 g). Food intake induced by atorvastatin is reduced to 229 g.

These findings suggest that the association Lipistase-PS induces a mechanism of action different from that stimulated by each compound alone. Indeed, greater food intake than other groups and reduced weight for the combination group leads to a higher energy expenditure that must be demonstrated by indirect calorimetry with a change in nutrient utilization in the enhancement of this energy expenditure (beta-oxidation, glucose catabolism . . . ).

These results compare to those obtained for the adipose tissue. The adiposity index is reported in FIG. 5. It clearly shows a reduction of this index with a loss of weight due to treatment with atorvastatin, but also with the combination Lipistase-PS (−35%, p=0.06), while the two compositions alone are less effective (−14%, ns). In FIG. 6, only treatments with atorvastatin and the combination Lipistase-PS induce significant changes in the distribution of white adipose tissue, with significant reductions in deep fat [(perirenal), (respectively −48% and −34%)], as well as surface fat [subcutaneous (respectively −57% and −43%) and epididymal fat (respectively −46% and −37%)] tissues.

Thus, this combination according to the invention prevents overweight induced by the diet rich in fat and cholesterol, similar to that observed.

Example 3

Figure 7:
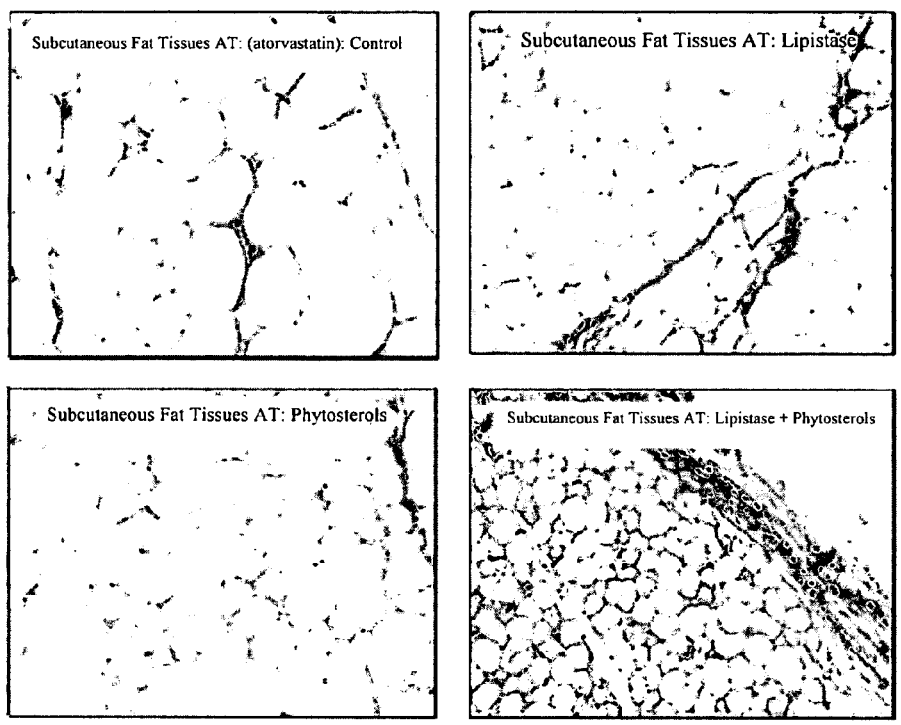
FIG. 7: Histological sections of subcutaneous adipose tissue after 12 weeks, HE staining, magnification ×20.

Demonstration of the Synergy of the Combination Lipistase-Phytosterols/Stanols on the Secretory Capacity of Adipose Tissue: Prevention of Tissue Inflammation and Preservation of Endocrine Function In FIG. 7, sections of subcutaneous adipose tissue in animals that received all treatments are represented. The morphology of these tissues shows significant differences, particularly in animals treated with the combination Lipistase-PS, with many small cells, whereas in the sections of control animals, the adipocytes are very large cells.

Sections of the adipose tissues of control animals show infiltration of macrophages between the adipocytes, these infiltrations are not visible in sections from animals treated with the combination Lipistase-PS.

Figure 8A:
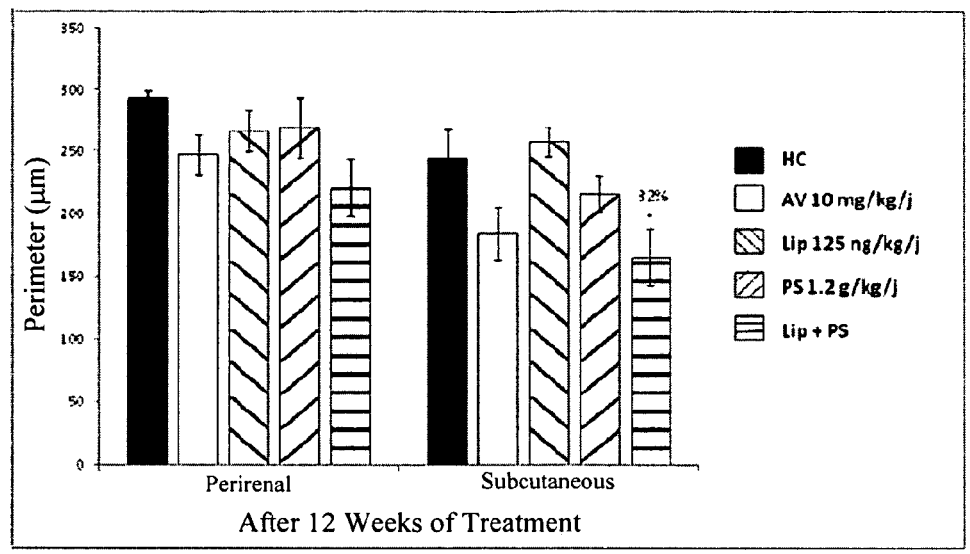
FIG. 8a: Morphometry of adipose tissue, perimeters of perirenal and subcutaneous adipocytes, percentage changes compared to controls HC (diet enriched in cholesterol), *p<0.05, n=12.
Figure 8B:
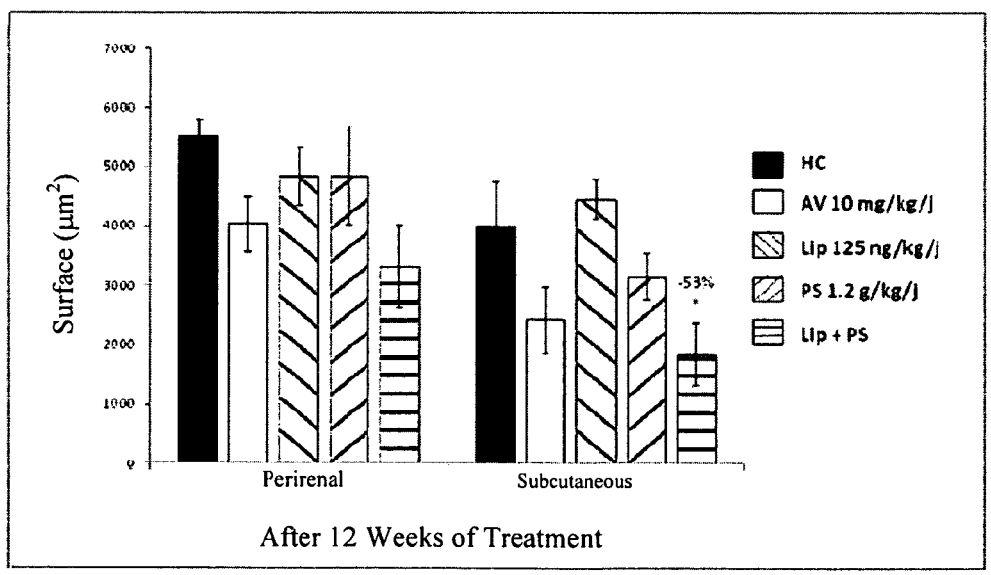
FIG. 8b: Morphometry of adipose tissue, surfaces of perirenal and subcutaneous adipocytes, percentage changes compared to controls HC (diet enriched in cholesterol), *p<0.05, n=12.

Moreover, considering morphometric data reported in FIGS. 8a and 8b, only the association Lipistase-PS induces significant changes in subcutaneous adipose tissue, with adipocytes of small perimeters and small areas, with reductions of −32% and −53% respectively.

It is well described in the literature that large adipocytes are representative of a state of chronic inflammation, the rates of secretion of cytokines such us IL6, IL8 and MCP1 are high, and the secretion of adiponectin is low (Cole et al , 2010; Gustafson, 2010).

Figure 5:
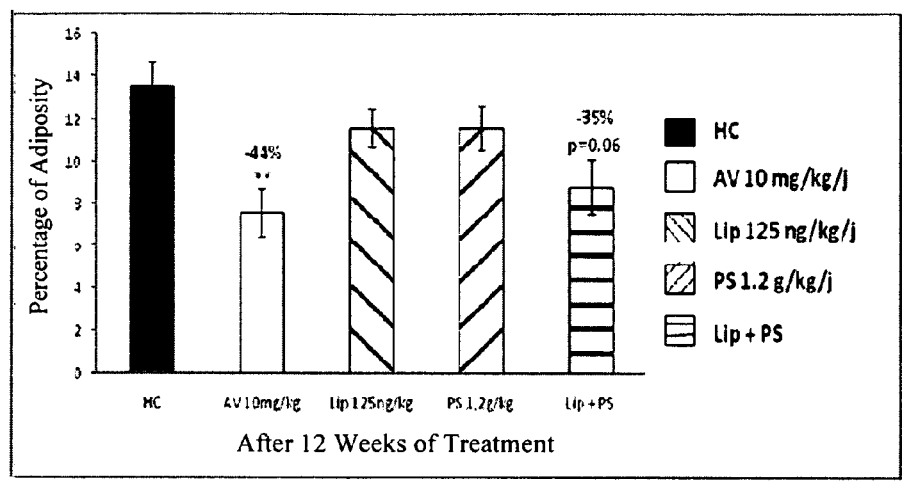
FIG. 5: Adiposity index after 12 weeks of treatment, expressed in %, and percentage changes compared to controls HC (diet enriched in cholesterol), **p<0.01, n=12.
Figure 6:
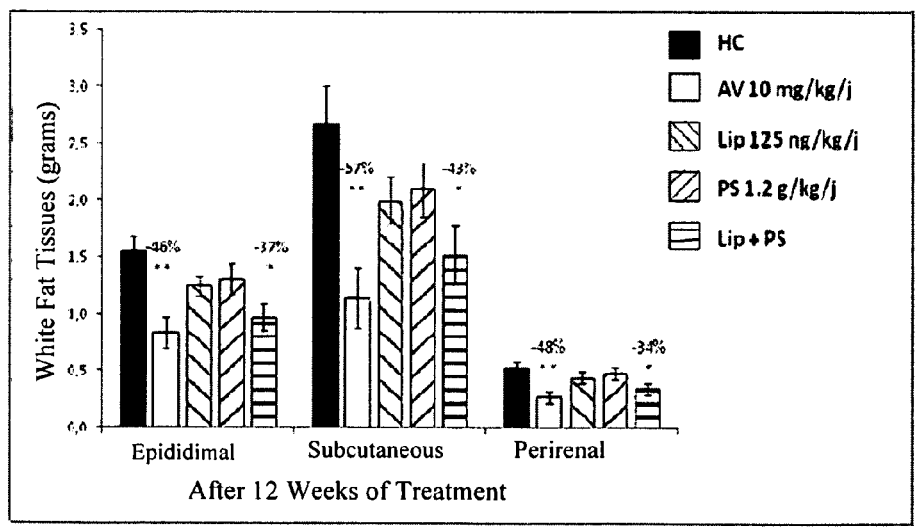
FIG. 6: Distribution of white adipose tissue after 12 weeks of treatment, expressed in g, and percentage changes compared to controls HC (diet enriched in cholesterol), **p<0.01, *p<0.05, n=12.
Figure 9:
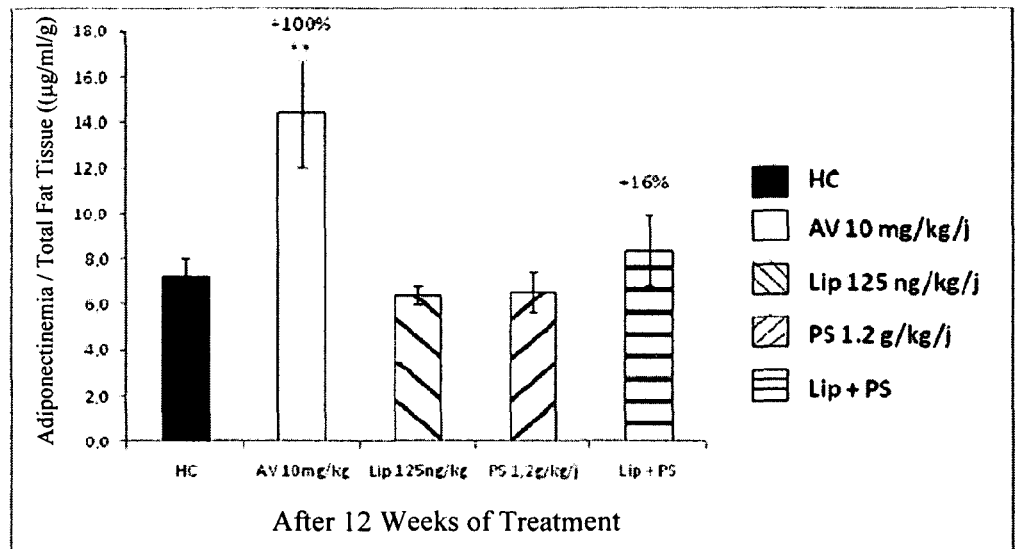
FIG. 9: Index of adiponectin secretion [adiponectin concentration (μg/ml)/mass of adipose tissue (g)], percentage changes compared to controls HC (diet enriched in cholesterol), **p<0.01, *p<0.05, n=12.

Thus in FIG. 9, the adiponectin secretion index by adipose tissue is significantly elevated by the reference and, to a lesser extent, by the association Lipistase-PS with an increase of 16% while the mass of adipose tissue decreased by an average of 39% (as shown in FIG. 5).

All these measures and findings clearly demonstrate that the combination of the Lipistase composition and PS reduces the development of body fat mass while keeping the endocrine function of adipose tissue in terms of adiponectin secretion, even enhancing it. In addition, the combination can limit the inflammatory process in the same adipose tissue, thus fighting the development of metabolic syndrome.

Example 4

Figure 10A:
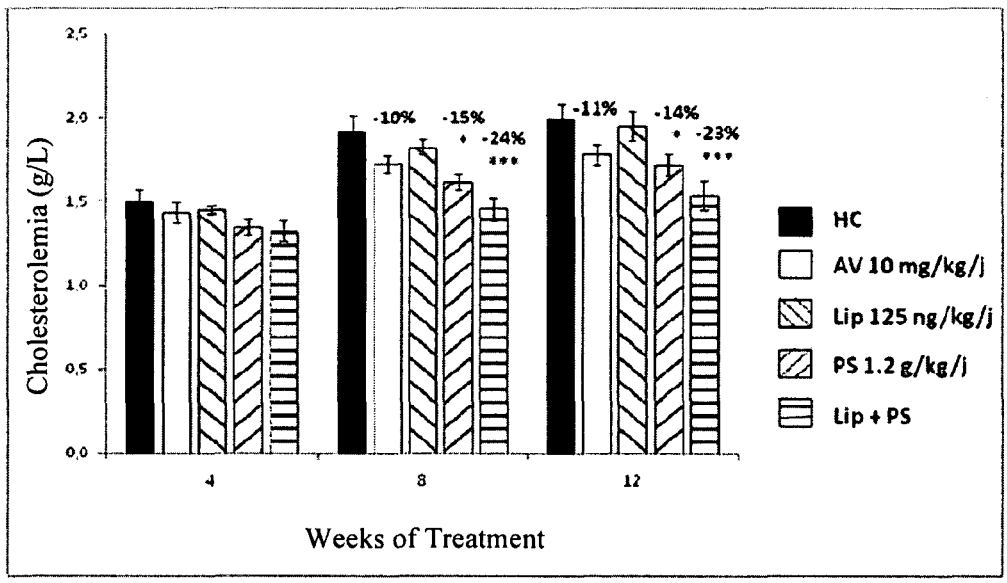
FIG. 10a: Changes in non-fasting cholesterol levels, percentage changes compared to controls HC (diet enriched in cholesterol), **p<0.01, *p<0.05, n=12.
Figure 10B:
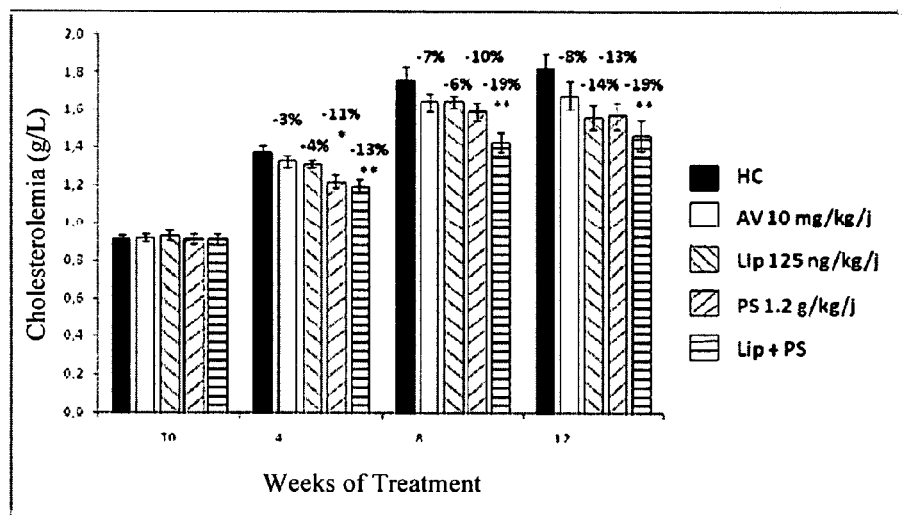
FIG. 10b: Changes in cholesterol after 4 h of fasting, percentage changes compared to controls HC (diet enriched in cholesterol), **p<0.01, *p<0.05, n=12.

Demonstration of the Synergy of the Combination Lipistase-Phytosterols on the Regulation of Lipid Homeostasis The evolution of the cholesterolemia is reported in FIG. 10a for non-fasting animals and in FIG. 10b for animals undergoing a 4-hour fasting period. Considering the results obtained when the animals are not fasting (FIG. 10a), Lipistase shows no effect on cholesterol in this particular case, while the PS significantly decreased cholesterolemia at just 8 weeks of treatment (−15%, *). But when PS were associated with the Lipistase composition, the effects observed on reducing cholesterol were significantly greater, until reaching a −24% reduction after 8 weeks of treatment, and stabilizing even after 3 months of treatment.

When animals are fasted for 4 hours (FIG. 10b), the effects of PS on cholesterol are much less marked (−11%, * at 4 weeks; −10%, ns at 8 weeks, and −13%, ns at 12 weeks). Concerning the Lipistase composition, the observed effects on cholesterol change over time (−4%, ns at 4 weeks −6%, ns at 8 weeks, and −14%, ns at 12 weeks), and were comparable after 12 weeks of treatment to those observed with the PS treatment. When the combination Lipistase-PS is given to animals, they show a significant reduction of cholesterol as soon as in the first month of treatment (−13%, *), further maintained and stabilized in the second and third months of treatment at −19% (*).

Figure 11A:
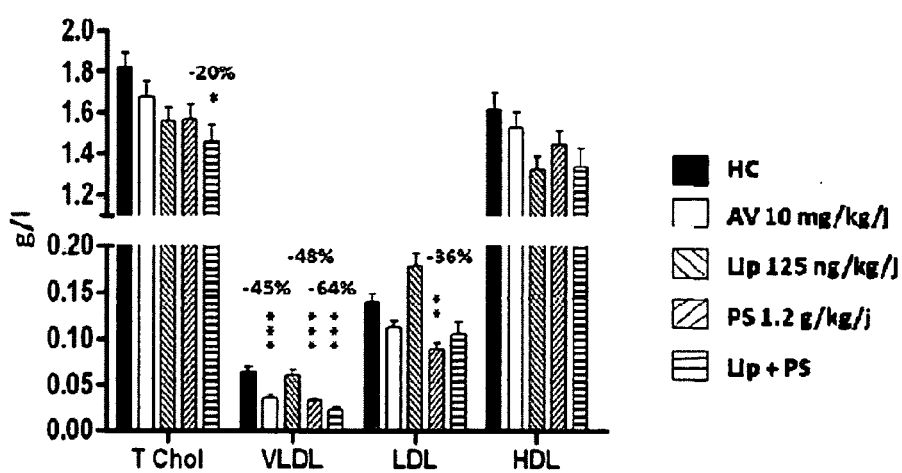
FIG. 11a: Distribution of total cholesterol in lipoproteins, percentage changes compared to controls HC (diet enriched in cholesterol), *p<0.001, p<0.01, *p<0.05, n=12.
Figure 11B:
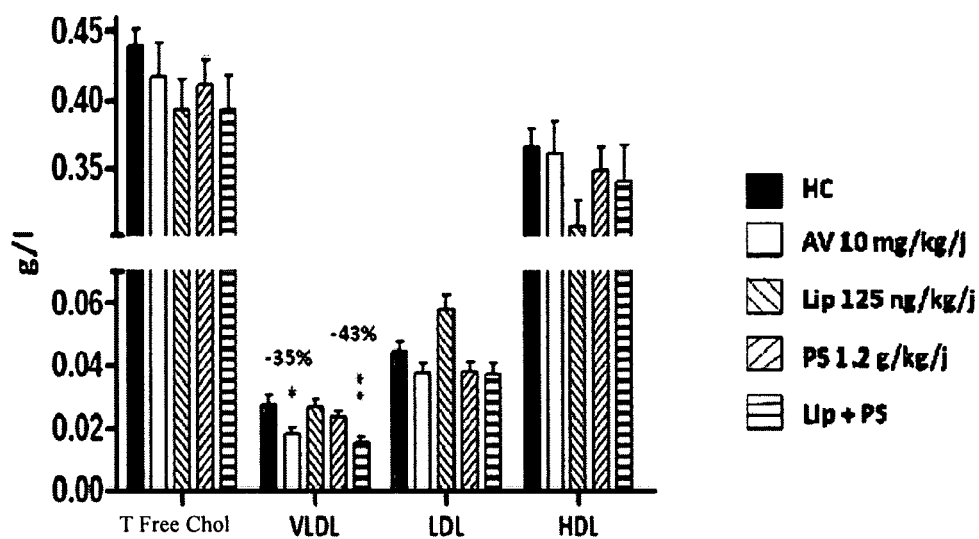
FIG. 11b: Distribution of free cholesterol in lipoproteins, percentage changes compared to controls HC (diet enriched in cholesterol), *p<0.001, p<0.01, *p<0.05, n=12.
Figure 11C:
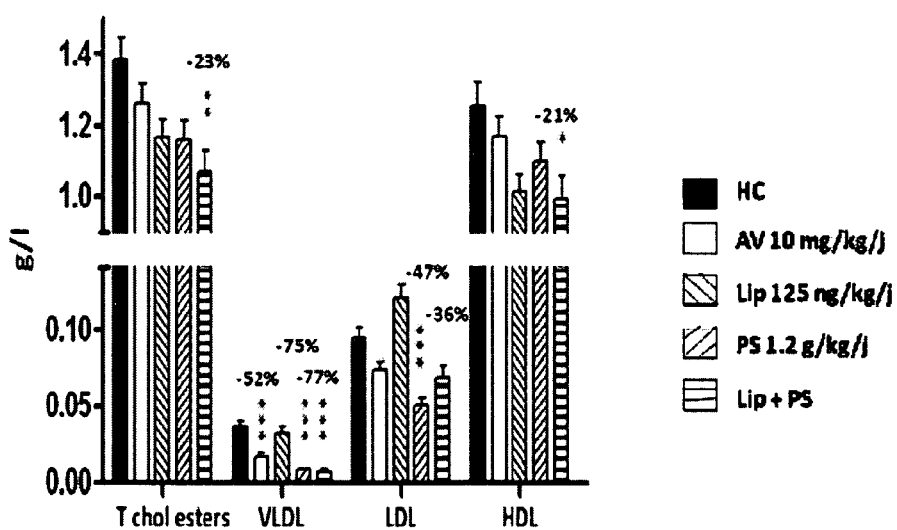
FIG. 11c: Distribution of cholesterol ester in lipoproteins, percentage changes compared to controls HC (diet enriched in cholesterol), *p<0.001, p<0.01, *p<0.05, n=12.

If one focuses on the distribution of total cholesterol in different lipoproteins, one will find that the strongest effects emerge with the association Lipistase–PS, −64% for VLDL (FIG. 11a), while the PS alone induced only a reduction of −48% in this fraction. The association is also very effective in reducing the free (most atherogenic) cholesterol in VLDL with a reduction of −43%, atorvastatin reaching only −35% while Lipistase alone and PS alone have no significant effects (FIG. 11b). Finally, it is clear that the combination potentiates the reduction of cholesterol esters (FIG. 11c) in all lipoproteins with reductions of −77% in VLDL, −36% in LDL, and −21% in HDL.

Figure 12:
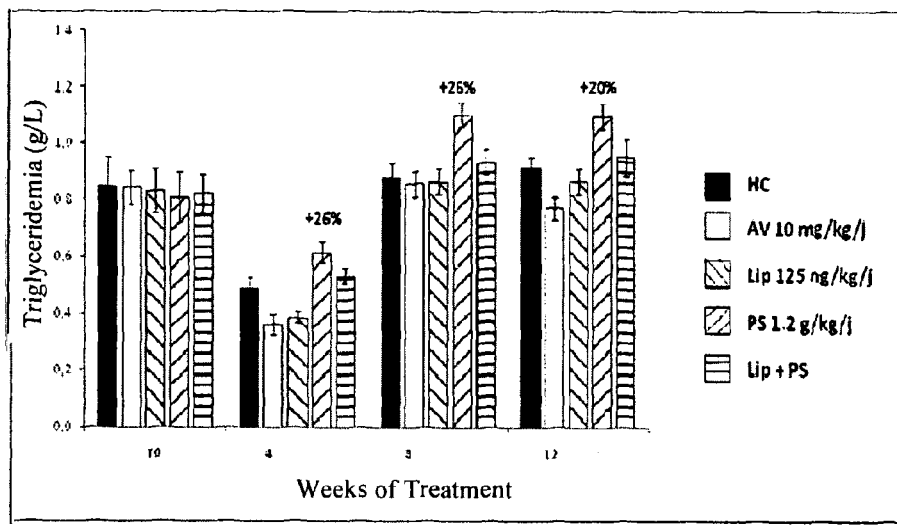
FIG. 12: Changes in triglyceride levels after 4 h of fasting, percentage changes compared to controls HC (diet enriched in cholesterol), n=12.

Results obtained on triglyceridemia in animals fasted for 4 hours (FIG. 12) show in this mouse model an effect of stimulation of the triglyceride rate by PS as soon as the first month of treatment with a 26% increase, this effect remaining stable for the duration of treatment. This observation must be related to the capacity of LXR agonists (Chuu et al, 2007) of PS; these agonists are known to induce the production of triglycerides in rodents. However, when Lipistase is administered in conjunction with PS, the stimulatory effect of triglyceridemia is countered because the values obtained for the combination are quite comparable to those of control animals.

Thus, the combination can potentiate the regulatory effect on cholesterolemia, on one hand, over time by an earlier control than with the individual components, and, on the other hand, in intensity by solidly maintaining a greater decrease than that observed with PS alone and Lipistase alone. In addition, by reducing the accumulation of different fractions of cholesterol in both LDL and VLDL, the combination may be a good element of prevention against the development of atherosclerosis. The opposite effects on triglycerides show an improvement in the safety and tolerance of the combination Lipistase-PS versus PS alone, in addition to the regulation of lipid homeostasis.

Example 5

Demonstration of the Synergy of the Association Lipistase-Phytosterols (PS) on the Prevention of Insulin Resistance Animals fed with diets enriched in fat and cholesterol gradually develop metabolic syndrome, and this effect is reported in numerous publications including the latest ones: Wuesst et al (2009), Bie et al (2010), and Chen et al (2010). This development is characterized, among other things, by an increase in glycemia and insulinemia, reflecting the progressive insensitivity of peripheral tissues.

Figure 13:
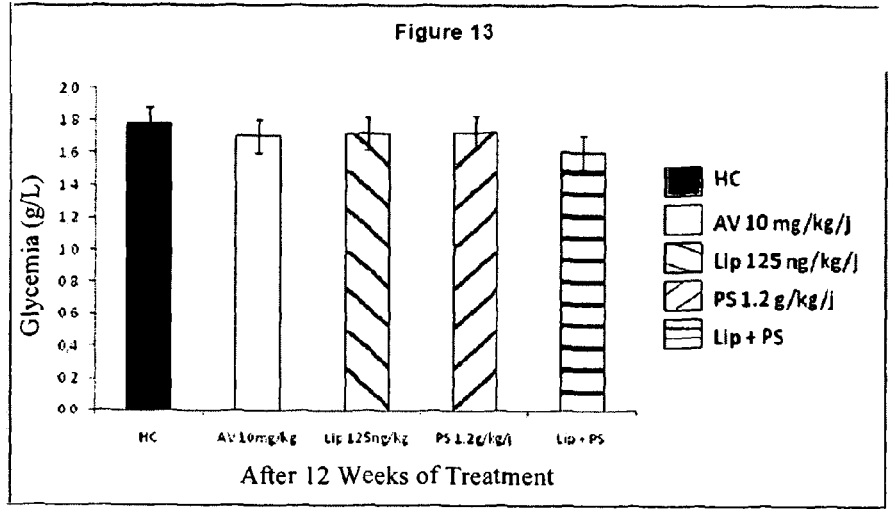
FIG. 13: Quantification of non-fasting blood glucose levels after 12 weeks of treatment, n=12.
Figure 14:
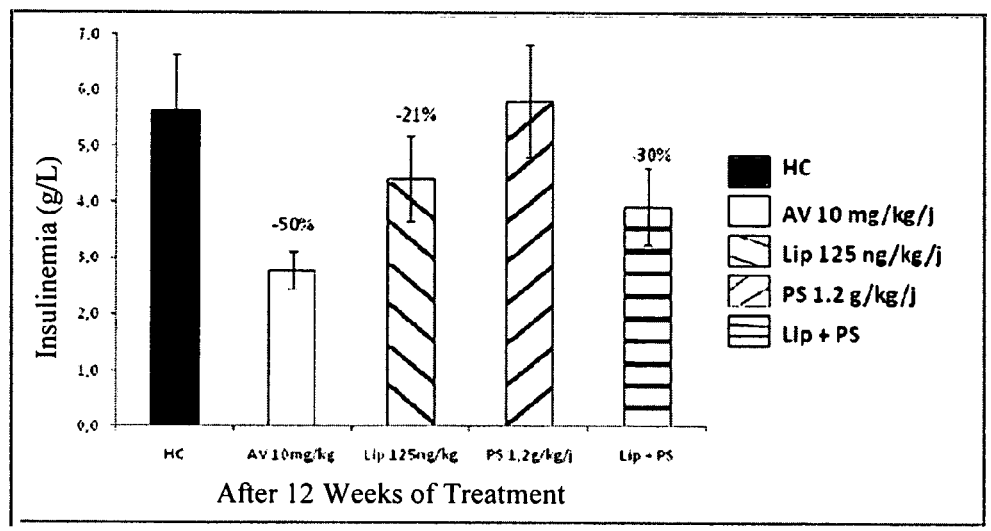
FIG. 14: Quantification of non-fasting insulin levels after 12 weeks of treatment, percentage changes compared to controls HC (diet enriched in cholesterol), n=12.

FIG. 13 and FIG. 14 respectively report values of glycemia (g/l) and insulinemia (ng/ml). The average glycemia levels in the control group is 1.78±0.10 g/l. The treatments did not differ significantly, but blood glucose of animals receiving the combination Lipistase-PS display an average decrease of 1.60±0.07 g/l.

When considering insulin levels measured in all treated animals, atorvastatin lowers insulin levels by −50%, reducing the value of the circulating rate to 2.79±0.33 ng/ml versus 5.64±0.99 ng/ml for the control animals. Lipistase treatment alone induced a more moderate reduction of −21% (4.43±0.76 ng/ml) while the combination Lipistase-PS seems more powerful with a reduction of −30% (3.93±0.68 ng/ml). PS are without effect on blood sugar as well as insulin levels.

It is clear that atorvastatin reduces insulin resistance, as a reduced rate of 50% seems sufficient to keep blood sugar at the same level than that of the control animals. Lipistase reduces to a lesser degree peripheral insulin resistance with a moderate reduction in insulin level (−21%) without significant change in blood sugar. However the combination of Lipistase and PS induces a higher sensitivity of peripheral tissues, since this treatment not only reduces insulin levels by −30%, but also glucose levels. This therefore reflects a potentiating effect on the ability of peripheral tissues to consume circulating glucose. Therefore, the combination Lipistase-PS improves peripheral sensitivity to glucose and prevents insulin resistance induced by fatty diet.

Example 6

Figure 15:
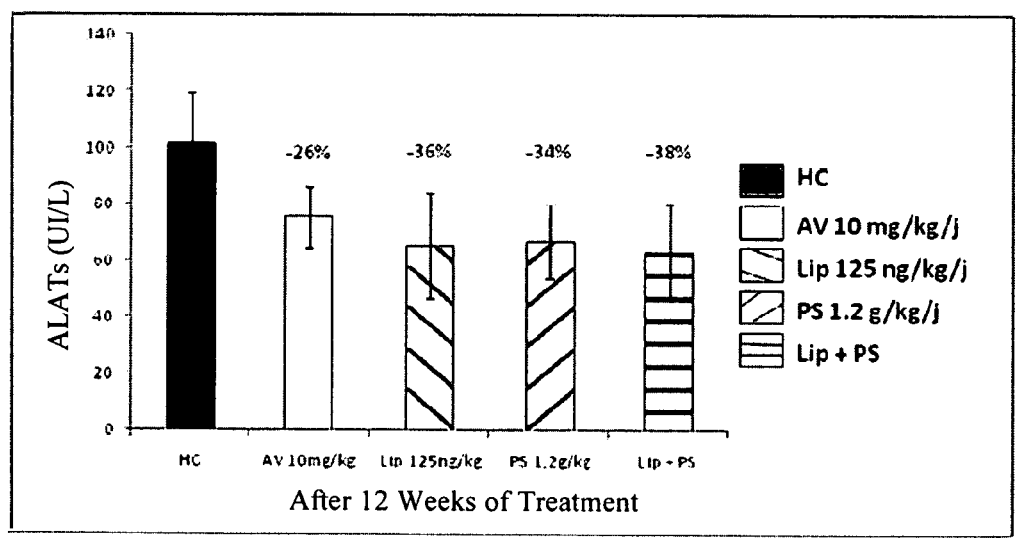
FIG. 15: Measurement of ALAT in serum of non-fasting animals after 12 weeks of treatment, percentage changes compared to controls HC (diet enriched in cholesterol), n=12.
Figure 16:
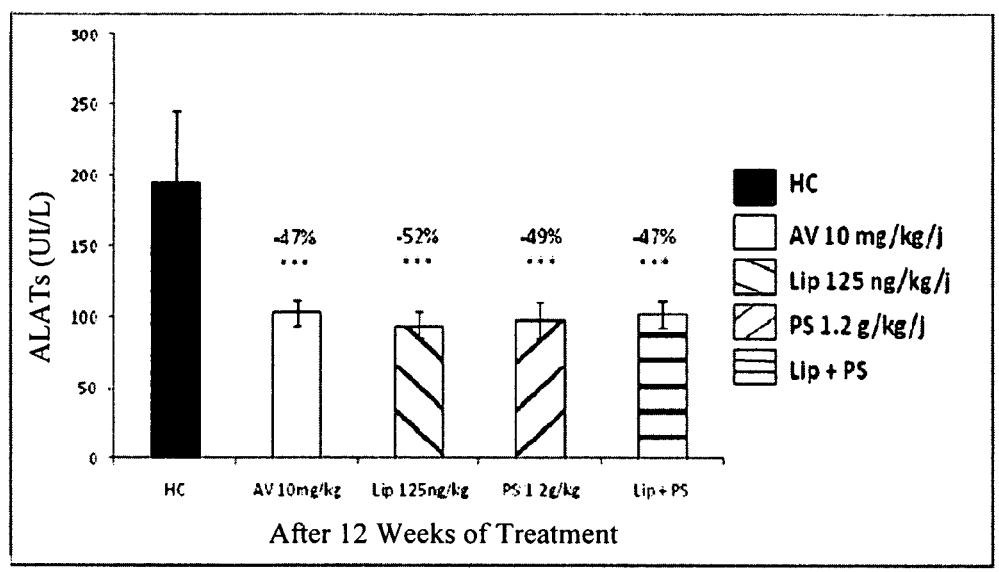
FIG. 16: Measurement of ASAT in serum of non-fasting animals after 12 weeks of treatment, percentage changes compared to controls HC (diet enriched in cholesterol), ***p<0.001, n=12.

Description of the Synergy of the Combination Lipistase-Phytosterols (PS) on the Prevention of Hepatic Steatosis In addition to insulin resistance, consumption of fat-enriched diet induces hepatic steatosis (mainly triglyceride overload). The plasma parameters reflecting a "suffering" liver are the ASAT and ALAT, which are elevated in the control animals of our experiment. With different treatments, values are effectively reduced in a non-differential way between the four treatments (as an average −30% for ALAT and −50% for ASAT): FIGS. 15 and 16.

Figure 17:
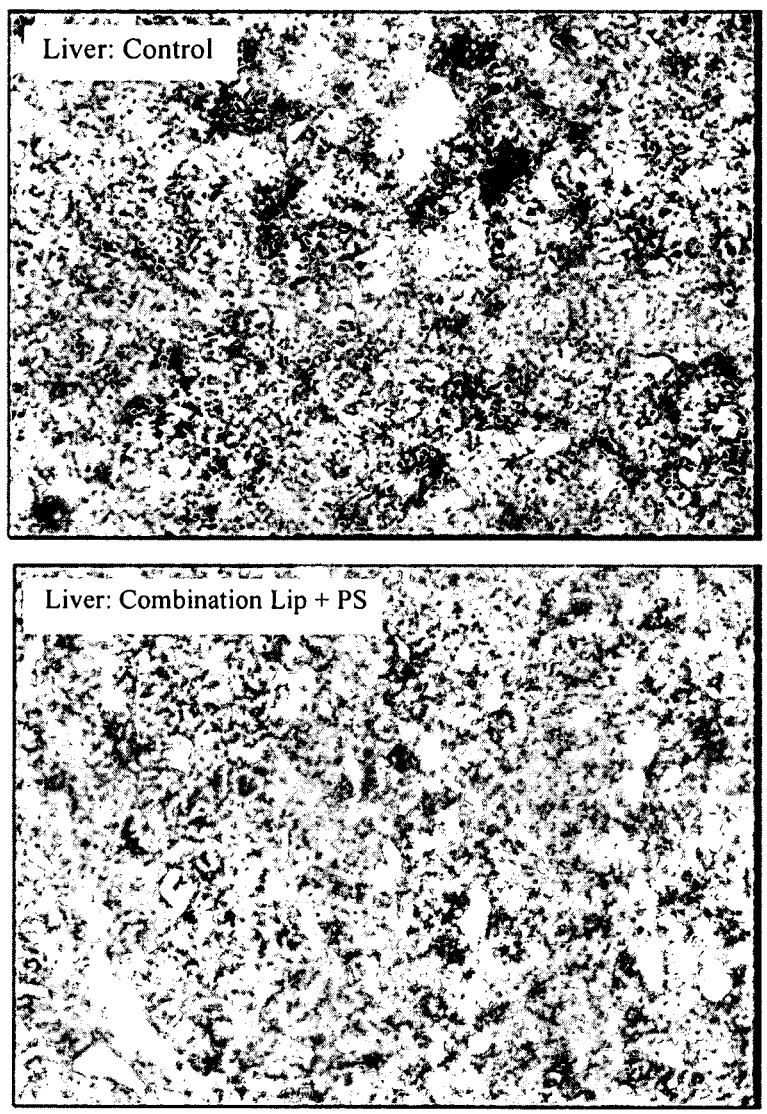
FIG. 17: Histological sections of the liver median lobe after 12 weeks of treatment, red oils staining for fats marking, magnification X 20.
Figure 18:
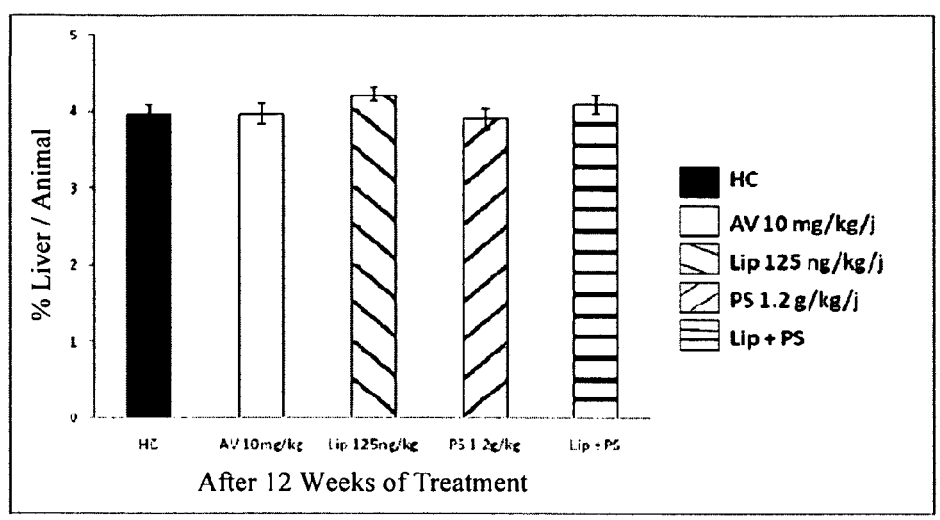
FIG. 18: Liver weight/body weight ratio in percentage after 12 weeks of treatment, n=12.

In FIG. 17, liver slices were reported after staining with red oils to highlight the accumulation of lipids in hepatocytes. These accumulations appear as small black granules that are clearly visible in the photo showing a liver section of the control animals. Whatever sections observed in animals treated with the combination Lipistase-PS, no animal shows accumulation of lipid in sections, while some animals show some accumulation when treated with Lipistase alone or with PS alone. These effects are interesting even if the ratio liver weight/body weight is not modified (FIG. 18). Thus, the combination of PS with Lipistase prevents the development of steatosis in liver while maintaining liver tolerance.

References

Clifton P M, Noakes M, Ross D, Fassoulakis A, Cehun M, Nestel P, "*High dietary intake of phystosterol esters decreases carotenoids and increases plasma plant sterol levels with no additional cholesterol lowering*", J Lipid Res, 2004, 45, 1493-1499.
Denke M A, "*Lack of efficacy of low-dose sitostanol therapy as an adjunct to a cholesterol-lowering diet in men with moderate hypercholesterolemia*", Am J Clin Nutr, 1995, 61, 392-396.
Katan M B, Grundy S M, jones P, Law M, Miettinen T, Paoletti R, "*Efficacy and safety of plants stanols and sterols in the management of blood cholesterol levels*", Mayo Clin Proc, 2003, 78, 965-078.
Trautwein E A, Duchateau G S, Lin Y G, Mel'nikov S M, Molhuizen H O F, Ntanios F Y, "*Proposed mechanisms of cholesterol-lowering action of plant sterols*" Eur J Lipid Sci Technol, 2003, 105, 171-185.
Bie J, Zhao B, Song J, Ghosh S; <<Improved insulin sensitivity in high-cholesterol fed LDLR−/− mice with macrophage-specific transgenic expression of cholesteryl ester hydrolase: role of macrophage inflammation and infiltration into adipose tissue>>; J Biol Chem; 2010; Feb. 26.
Chen X, Yu Q Q, Zhu Y H, Bi Y, Sun W P, Liang H, Cai M Y, He X Y, Weng J P; <<insulin therapy stimulates lipid synthesis and improve endocrine functions of adipocytes in dietary obese C57bl/6 mice>>; Acta Pharmacol Sin; 2010; 31(3):341-346.
Chuu C P, Kokontis J M, Hiipakka R A, Liao S, <<modulation of LXR signaling as novel therapy for prostate cancer>>; J Biomed Sci, 2007, 14, 543-553.
Cole B K, Keller S R, Wu R, Carter J D, Nadler J L, Nunemaker C S, <<Valsartan protects pancreatic islets and adipose tissue from the inflammatory and metabolic consequences of a high fat diet in mice>>; Hypertension; 2010; 55(3), 715-721.
Gustafson B, <<Adipose tissue, inflammation and atherosclerosis>>, J Atheroscler Thromb, 2010 Feb. 3
Wueest S, Rapold R A, Rytka J M, Schoenle E J, Konrad D, <<Basal lipolysis, not the degree of insulin resistance, differentiates large from small isolated adipocytes in high-fat fad mice>>; Diabetologia; 2009; 52:541-546.

The invention claimed is:

1. A nutraceutical and/or food composition designed to regulate lipid metabolism in humans and animals characterized in that said composition comprises, per 100g or 100mL, the combination of:
7µg to 700µg of at least two plant oils selected rapeseed oil, olive oil, grape seed oil, and evening primrose oil,
10µg to 1000µg of positively charged minerals selected from sodium, magnesium, and calcium,
10µg to 1000µg of metals selected from zinc and iron,
7µg to 700µg of yeast or yeast extracts originating from genus *Saccharomuces*, characterized in that said yeasts or yeast extracts are enriched with selenium,
7µg to 700µg of mycelium or extracts from Shiitake,
6µg to 600µg of at least two plant extracts from plants selected from samphire, garlic, and grapevine,
8µg to 800µg of at least one vitamin selected from vitamins A, B1, B9, C, E, F, and PP,
7µg to 700µg of animal oil and Copra oil, and
6µg to 600µg of at least one alga selected from *Palmaria palmata, Chondrus crispus*, and *Fucus vesiculosus*, in combination with at least one selected from phytosterols, stanols and mixtures thereof, and
a pharmaceutical acceptable excipient.

2. The nutraceutical and/or food composition designed to regulate lipid metabolism in humans and animals according to claim 1 wherein the animal oil consists of cold water fish oil.

3. The nutraceutical and/or food composition designed regulate lipid metabolism in humans and animals according to claim 1, wherein said composition contains at least two vitamins selected from vitamins A, B1, B9, C, E, F, and PP.

4. The nutraceutical and/or food composition according to claim 1, wherein said composition comprises per 100g or 100mL:
7µg to 700µg of rapeseed oil, olive oil, grape seed oil, and evening primrose oil,
10µg to 1000µg of sodium, magnesium, and calcium,
10µg to 1000µg of zinc and iron,
7µg to 700µg of yeast or yeast extracts from *Saccharomyces cerevisiae*, enriched with selenium,
7µg to 700µg of mycelium or mycelium extracts from Shiitake,
6µg to 600µg of samphire, garlic, and grapevine,
8µg to 800µg of vitamins A, B1, B9, C, E, F, and PP,
7µg to 700µg of cold water fish oil and Copra oil, and
6µg to 600µg *Palmaria palmata, Chondrus crispus*, and *Fucus vesiculosus*,
in combination with the at least one selected from phytosterols, stanols and mixtures thereof, and
the pharmaceutical acceptable excipient.

5. The nutraceutical and/or food composition according to claim 1, wherein said composition further comprises excipients or additives.

6. The nutraceutical and/or food composition according to claim 1, wherein said phytosterols, stanols (PS) used are selected from the group including cholesterol, brassicasterol, campesterol, campestanol, stigmasterol, beta-sitosterol, beta-sitostanol, D5 avenasterol, D7 stigmastenol, D7 avenasterol, and combinations and mixtures thereof.

7. The nutraceutical and/or food composition according to claim 1, wherein the composition is in the form of a solid, liquid, oil, gel, strip, paste, powder, or gum.

8. The nutraceutical and/or food composition according to claim 1, wherein the composition is suitable for oral administration.

9. The nutraceutical and/or food composition according to claim 1, wherein said composition is a medicament.

10. The nutraceutical and/or food composition according to claim 1, wherein the yeast or yeast extracts are from *Saccharomyces cerevisiae*.

11. The nutraceutical and/or food composition according to claim 5, wherein the additives are selected from sweeteners, stabilizing agents, preservatives, dyes, emulsifiers or gelling agents, flavor enhancers, acidifiers, and flavors.

12. A method of preparing a food additive designed for the regulation of lipid homeostasis or for the prevention of a condition selected from metabolic syndrome, cancer risks, cardiovascular diseases, dyslipidemia, hypertension, progression of atherosclerosis, obesity, hyperglycemia, macular degeneration in diabetes, and neurodegenerative diseases in humans and animals, the method comprising:

using the nutraceutical and/or food composition according to claim 1 in a food or drink.

13. A method of preparing a medicament designed for the treatment or prevention of a condition selected from metabolic syndrome, cancer risks, cardiovascular diseases, dyslipidemia, hypertension, progression of atherosclerosis, obesity, hyperglycemia, macular degeneration in diabetes, neurodegenerative diseases, and regulation of lipid homeostasis in humans and animals, the method comprising:

using the nutraceutical and/or food composition according to claim 1 in the medicament.

* * * * *